US012702360B2

(12) United States Patent
Shute et al.

(10) Patent No.: US 12,702,360 B2
(45) Date of Patent: Aug. 11, 2026

(54) HEART SOUND BASED SYNCOPE DETECTION

(71) Applicant: Cardiac Pacemakers, Inc., St. Paul, MN (US)

(72) Inventors: Jonathan Bennett Shute, Eagan, MN (US); Pramodsingh Hirasingh Thakur, Woodbury, MN (US); Ashley Moriah Jensen, Apple Valley, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 456 days.

(21) Appl. No.: 18/098,457

(22) Filed: Jan. 18, 2023

(65) Prior Publication Data

US 2023/0233159 A1 Jul. 27, 2023

Related U.S. Application Data

(60) Provisional application No. 63/302,432, filed on Jan. 24, 2022.

(51) Int. Cl.

*A61B 5/00* (2006.01)
*A61B 5/0205* (2006.01)
*A61B 7/04* (2006.01)
*A61B 5/11* (2006.01)

(52) U.S. Cl.

CPC .......... *A61B 5/7282* (2013.01); *A61B 5/0205* (2013.01); *A61B 5/7275* (2013.01); *A61B 7/04* (2013.01); *A61B 5/1116* (2013.01)

(58) Field of Classification Search

None

See application file for complete search history.

(56) References Cited

U.S. PATENT DOCUMENTS

| | | | | |
|---|---|---|---|---|
| 7,115,096 | B2 | 10/2006 | Siejko et al. | |
| 7,853,327 | B2 | 12/2010 | Patangay et al. | |
| 8,498,703 | B2 | 7/2013 | Spinelli et al. | |
| 8,761,878 | B2 | 6/2014 | Sanders | |
| 2006/0253042 | A1* | 11/2006 | Stahmann | G16H 40/67 607/18 |
| 2018/0325466 | A1* | 11/2018 | An | A61B 5/346 |
| 2019/0008467 | A1* | 1/2019 | Averina | A61B 5/746 |

* cited by examiner

*Primary Examiner* — Ankit D Tejani
(74) *Attorney, Agent, or Firm* — Nelson Mullins Riley & Scarborough LLP

(57) ABSTRACT

Systems and methods are disclosed to detect a potential syncope event using cardiac acceleration information of a patient and to transition a medical device from a first low-power mode to a second high-power mode in response to the detected potential syncope event.

20 Claims, 5 Drawing Sheets

HEART SOUND BASED SYNCOPE DETECTION

CLAIM OF PRIORITY

This application claims the benefit of priority under 35 U.S.C. § 119(e) of U.S. Provisional Patent Application Ser. No. 63/302,432, filed on Jan. 24, 2022, which is herein incorporated by reference in its entirety.

TECHNICAL FIELD

This document relates generally to medical devices comprising an accelerometer and more particularly to heart sound based syncope detection.

BACKGROUND

Implantable medical devices (IMDs), such as cardiac rhythm management (CRM) devices, can be used to monitor, detect, or treat various cardiac conditions associated with a reduced ability of a heart to sufficiently deliver blood to a body. In some cases, heart conditions may lead to rapid, irregular, or inefficient heart contractions, etc. To alleviate one or more of these conditions, various medical devices can be implanted in a patient's body to monitor heart activity or to provide electrical stimulation to optimize or control contractions of the heart.

Heart failure (HF) is a reduction in the ability of the heart to deliver enough blood to meet bodily needs. Heart failure patients commonly have enlarged heart with weakened cardiac muscles, resulting in reduced contractility and poor cardiac output of blood. Typical signs of heart failure include shortness of breath, fatigue, weakness, pulmonary congestion, edema, etc.

Syncope is a temporary loss of consciousness caused by a fall in blood pressure, reducing oxygen supply to the brain. The most common type of syncope is neurally mediated syncope (NMS), where the part of the nervous system that regulates blood pressure and heart rate malfunctions in response to a trigger, such as emotional stress or pain. NMS typically occurs while standing, and is often preceded by a sensation of warmth, nausea, lightheadedness, tunnel vison, or visual disturbances. Placing the patient in a reclining position often restores blood flow and consciousness, ending the episode. Subcategories of NMS include situational syncope, often related to certain physical functions, such as coughing, laughing, or swallowing, carotid sinus syndrome (CSS), an abnormal response to carotid massage, and vasovagal syncope (VVS), a response to a sudden drop in blood flow to the brain.

Other types of syncope include orthostatic syncope, caused by a postural decrease in blood pressure that reduces blood flow to the cerebrum, and cardiac syncope, caused by various heart conditions including cardiac arrhythmias (e.g., bradycardia or tachycardia) or structural disorders, such as aortic stenosis, etc.

SUMMARY

Systems and methods are disclosed to detect a potential syncope event using cardiac acceleration information of a patient and to transition a medical device from a first low-power mode to a second high-power mode in response to the detected potential syncope event.

An example (e.g., "Example 1") of subject matter (e.g., a medical device system) may comprise a signal receiver circuit configured to receive cardiac acceleration information of a patient and an assessment circuit configured to detect a potential syncope event using the cardiac acceleration information of the patient, and to transition a medical device of the medical device system from a first low-power mode to a second high-power mode in response to the detected potential syncope event.

In Example 2, the subject matter of Example 1 may optionally be configured such that the signal receiver circuit is configured to receive cardiac electrical information of the patient and the assessment circuit is configured to detect the potential syncope event using the cardiac acceleration information and the cardiac electrical information of the patient.

In Example 3, the subject matter of any one or more of Examples 1-2 may optionally be configured such that the cardiac acceleration information comprises heart sound information of the patient, the cardiac electrical information of the patient comprises heart rate information of the patient, and the assessment circuit is configured to detect the potential syncope event using an increase in first heart sound (S1) information of the patient greater than a first threshold and an increase in the heart rate information of the patient greater than a second threshold.

In Example 4, the subject matter of any one or more of Examples 1-3 may optionally be configured such that assessment circuit is configured to detect an indication of a neurally mediated syncope (NMS) event using a decrease in second heart sound (S2) information of the patient greater than a third threshold in a first time period following the detected potential syncope event.

In Example 5, the subject matter of any one or more of Examples 1~4 may optionally be configured such that the assessment circuit is configured to detect the indication of the NMS event using the decrease in S2 information of the patient greater than the third threshold and a decrease in the S1 information of the patient greater than a fourth threshold in the first time period following the detected potential syncope event, and a subsequent decrease in the heart rate information greater than a fifth threshold in a second time period following the first time period.

In Example 6, the subject matter of any one or more of Examples 1-5 may optionally be configured such that the assessment circuit is configured to trigger a patient alert indicative of the detected indication of the NMS event and a patient inquiry to receive patient feedback of the detected indication of the NMS event in response to the detected indication of the NMS event.

In Example 7, the subject matter of any one or more of Examples 1-6 may optionally include a therapy circuit configured to alter or provide one of a drug therapy or a pacing therapy in response to the detected indication of the NMS event.

In Example 8, the subject matter of any one or more of Examples 1-7 may optionally be configured such that the signal receiver circuit is configured to receive activity or posture information of the patient and the assessment circuit is configured to detect a high risk syncope position of the patient using the activity or posture information of the patient, and in response to the detected high risk syncope position, to detect the potential syncope event using an increase in the cardiac acceleration information greater than a first threshold and an increase in the cardiac electrical information greater than a second threshold.

In Example 9, the subject matter of any one or more of Examples 1-8 may optionally be configured such that the assessment circuit is configured to detect the high risk syncope position of the patient as: a detected change in patient posture from a horizontal thoracic position to a vertical thoracic position; or a detected vertical thoracic position and patient activity information below an activity threshold.

In Example 10, the subject matter of any one or more of Examples 1-9 may optionally be configured such that the first low-power mode comprises an ambulatory monitoring mode, the second high-power mode comprises a higher-power monitoring mode including storing received cardiac acceleration information and the received cardiac electrical information in long-term storage, and the medical device comprises an implantable medical device comprising the signal receiver circuit and the assessment circuit.

An example (e.g., "Example 11") of subject matter (e.g., a method) may comprise receiving, using a signal receiver circuit, cardiac acceleration information of a patient; detecting, using an assessment circuit, a potential syncope event using the cardiac acceleration information of the patient; and transitioning, using the assessment circuit, a medical device from a first low-power mode to a second high-power mode in response to the detected potential syncope event.

In Example 12, the subject matter of any one or more of Examples 1-11 may optionally include receiving, using the signal receiver circuit, cardiac electrical information of the patient, wherein detecting the potential syncope event comprises using the cardiac acceleration information and the cardiac electrical information of the patient.

In Example 13, the subject matter of any one or more of Examples 1-12 may optionally be configured such that the cardiac acceleration information comprises heart sound information of the patient, the cardiac electrical information of the patient comprises heart rate information of the patient, and detecting the potential syncope event comprises using an increase in first heart sound (S1) information of the patient greater than a first threshold and an increase in the heart rate information of the patient greater than a second threshold.

In Example 14, the subject matter of any one or more of Examples 1-13 may optionally include detecting, using the assessment circuit, an indication of a neurally mediated syncope (NMS) event using a decrease in second heart sound (S2) information of the patient greater than a third threshold in a first time period following the detected potential syncope event.

In Example 15, the subject matter of any one or more of Examples 1-14 may optionally be configured such that detecting the indication of the NMS event comprises using the decrease in S2 information of the patient greater than the third threshold and a decrease in the S1 information of the patient greater than a fourth threshold in the first time period following the detected potential syncope event, and using a subsequent decrease in the heart rate information greater than a fifth threshold in a second time period following the first time period.

In Example 16, the subject matter of any one or more of Examples 1-15 may optionally include triggering, using the assessment circuit, a patient alert indicative of the detected indication of the NMS event and a patient inquiry to receive patient feedback of the detected indication of the NMS event in response to the detected indication of the NMS event.

In Example 17, the subject matter of any one or more of Examples 1-16 may optionally include altering or providing, using a therapy circuit, one of a drug therapy or a pacing therapy in response to the detected indication of the NMS event.

In Example 18, the subject matter of any one or more of Examples 1-17 may optionally include receiving, using the signal receiver circuit, activity or posture information of the patient, and detecting, using the assessment circuit, a high risk syncope position of the patient using the activity or posture information of the patient, wherein detecting the potential syncope event comprises using an increase in the cardiac acceleration information greater than a first threshold and an increase in the cardiac electrical information greater than a second threshold, further in response to the detected high risk syncope position.

In Example 19, the subject matter of any one or more of Examples 1-18 may optionally be configured such that detecting the high risk syncope position of the patient comprises using: a detected change in patient posture from a horizontal thoracic position to a vertical thoracic position; or a detected vertical thoracic position and patient activity information below an activity threshold.

In Example 20, the subject matter of any one or more of Examples 1-19 may optionally be configured such that the first low-power mode comprises an ambulatory monitoring mode, the second high-power mode comprises a higher-power monitoring mode including storing received cardiac acceleration information and the received cardiac electrical information in long-term storage, and the medical device comprises an implantable medical device comprising the signal receiver circuit and the assessment circuit.

In Example 21, subject matter (e.g., a system or apparatus) may optionally combine any portion or combination of any portion of any one or more of Examples 1-20 to comprise "means for" performing any portion of any one or more of the functions or methods of Examples 1-20, or at least one "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
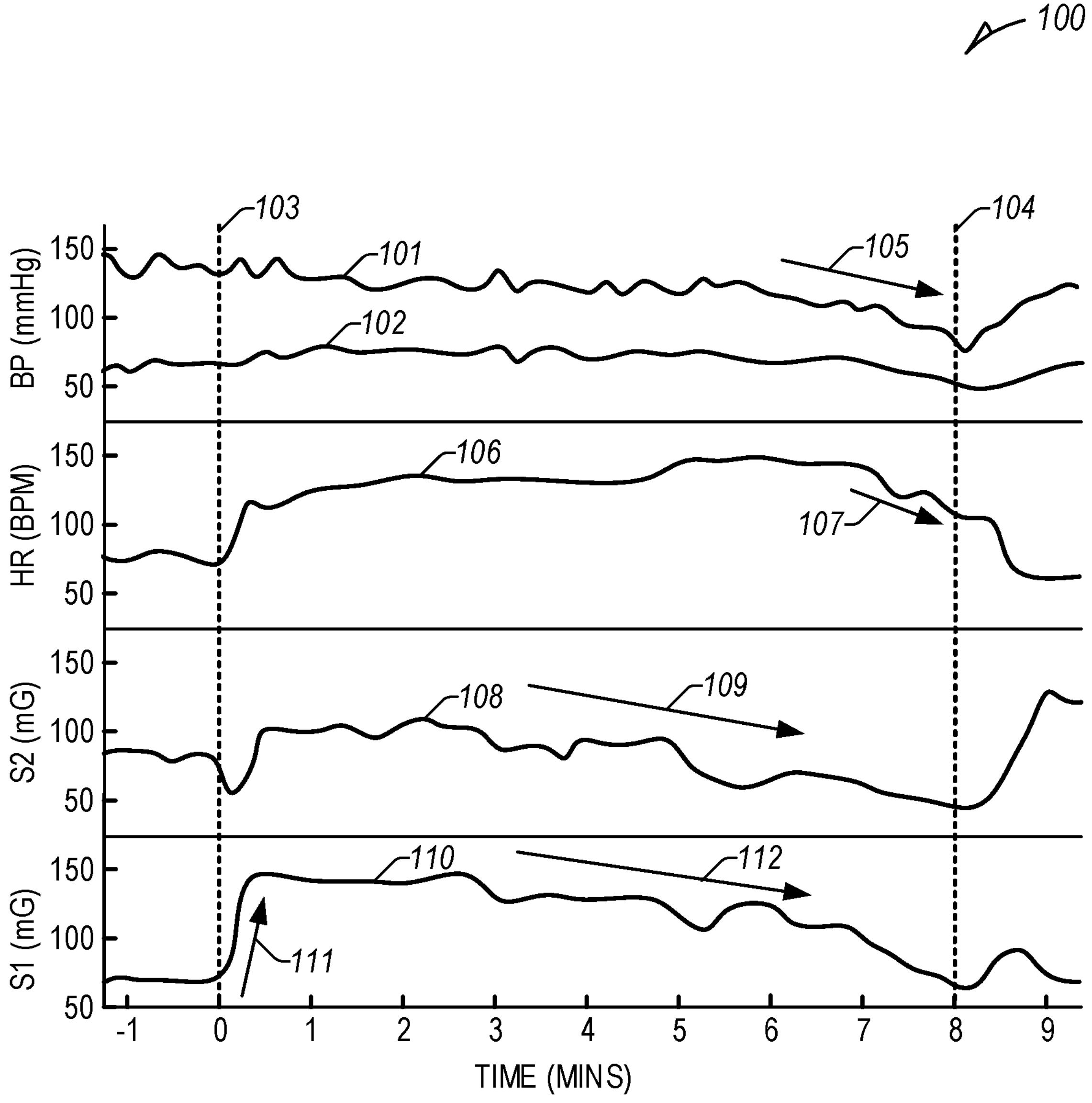
FIG. 1 illustrates a relationship between measured patient blood pressure, heart rate, and heart sound information during a tilt table test.

Implantable and ambulatory medical devices frequently contain one or more accelerometer sensors and corresponding processing circuits to determine and monitor patient acceleration information, such as, among other things, cardiac vibration information associated with blood flow or movement in the heart or patient vasculature (e.g., heart sounds, cardiac wall motion, etc.), patient physical activity or position information (e.g., patient posture, activity, etc.), respiration information (e.g., respiration rate, phase, breathing sounds, etc.), etc.

Heart sounds are recurring mechanical signals associated with cardiac vibrations or accelerations from blood flow through the heart or other cardiac movements with each cardiac cycle and can be separated and classified according to activity associated with such vibrations, accelerations, movements, pressure waves, or blood flow.

Heart sounds include four major features: the first through the fourth heart sounds (S1 through S4, respectively). The first heart sound (S1) is the vibrational sound made by the heart during closure of the atrioventricular (AV) valves, the mitral valve and the tricuspid valve, and the opening of the aortic valve at the beginning of systole, or ventricular contraction. The second heart sound (S2) is the vibrational sound made by the heart during closure of the aortic and pulmonary valves at the beginning of diastole, or ventricular relaxation. The third and fourth heart sounds (S3, S4) are related to filling pressures of the left ventricle during diastole. An abrupt halt of early diastolic filling can cause the third heart sound (S3). Vibrations due to atrial kick can cause the fourth heart sound (S4). Valve closures and blood movement and pressure changes in the heart can cause accelerations, vibrations, or movement of the cardiac walls that can be detected using an accelerometer or a microphone, providing an output referred to herein as cardiac acceleration information.

The present inventors have recognized, among other things, systems and methods to detect syncope using heart sound information, providing additional functionality to existing sensor systems. Moreover, the present inventors have recognized that specific combinations of heart sound information or specific heart sound parameters can provide earlier detection of a syncope event than traditional syncope detection using heart rate and blood pressure. Accordingly, heart sound based syncope detection can provide earlier indications of a syncope event, which enable existing medical devices and medical device systems to alter modes and change settings and parameters earlier to detect and capture valuable physiologic information leading up to and during a syncope event, such as by triggering additional sensing (e.g., blood pressure sensing, etc.), changing sensing modes (e.g., from a low-power mode to a high-power mode, altering periods of detection of certain parameters, etc.), lengthening the time period of parameters (e.g., detecting changes over longer time periods, such as multiple minutes, instead of seconds, etc.), increasing sampling frequency or resolution, increasing data storage periods, or providing or changing one or more therapy parameters to the patient based on the detected indication. Further, the detected indication can be used as an additional measure to improve existing blood pressure and heart rate based syncope detection, improving the sensitivity, specificity, or confidence of detected patient conditions, medical event storage, and alerts.

FIG. 1 illustrates a relationship 100 between measured patient physiologic information, including patient blood pressure (BP) (systolic blood pressure 101 and diastolic blood pressure 102), patient heart rate 106, and patient heart sound information (first heart sound (S1) information 110 and second heart sound (S2) information 108) for a patient diagnosed with NMS during a tilt table test, where a patient is moved from a horizontal (or near-horizontal) position quickly to an upright (vertical or near-vertical) position (e.g., commonly between 60 and 80 degrees relative to a horizontal zero degrees).

The tilt table test starts at time 0 minutes, at a first time 103, transitioning the patient from the horizontal position to the upright position. The measured patient physiologic information can be considered to be at or near respective baselines prior to the first time 103 with the patient in the horizontal position. The patient blood pressure and heart sound information both increase in response to the start of the tilt table test at the first time 103, but then decrease near the end of the tilt table test at a second time 104. If the tilt table test was not terminated, the patient would have lost consciousness.

After the first time 103, the systolic blood pressure 101 begins to slowly drop from a baseline prior to the first time 103 (e.g., about 140 mmHg) until approximately five-and-a-half minutes (e.g., about 125 mmHg), where the systolic blood pressure 101 begins to drop more sharply at a first position 105 until the tilt table test end at time 8 minutes, at the second time 104 (e.g., reaching about 90 mmHg at time 8 minutes), and continuing to drop shortly thereafter before recovering.

Conversely, after the first time 103, the diastolic blood pressure 102 begins to slowly rise from a baseline prior to the first time 103 (e.g., about 65 mmHg) for one minute (e.g., to about 80 mmHg), then staying roughly stable until approximately time five-and-a-half minutes before dropping until the tilt table test end at time 8 minutes, at the second time 104 (e.g., reaching about 50 mmHg at time 8 minutes), and continuing to drop shortly thereafter before recovering.

The patient heart rate 106 sharply rises from a baseline (e.g., about 75 bpm) for the first half minute (e.g., to about 115 bpm) after time 0 minutes, at the first time 103, then more slowly to a max at about time five-and-a-half minutes (e.g., about 150 bpm), then slowly dropping until time 7 minutes before a sharply decreasing at a second position 107 until the tilt table test end at time 8 minutes and continuing to drop thereafter to the previous baseline.

The present inventors have recognized, among other things, that the patient heart sound information, the S1 information 110 and the S2 information 108 (e.g., S1 and S2 amplitude, respectively), unexpectedly responds differently and earlier than patient heart rate and blood pressure to an upcoming syncope event. That is, patient heart sound information is not used here as a surrogate for blood pressure or heart rate information, per se, but rather, changes in patient heart sound information respond minutes earlier to an upcoming syncope event, enabling a number of alerts, device sensing, monitoring, storage, and therapy changes prior to a potential syncope event.

A technological problem exists in medical devices, that by the time physiological information indicates a possible upcoming event, valuable information has been lost, unable to be recorded. In low-power monitoring modes, ambulatory medical devices powered by a rechargeable or non-rechargeable battery, have to make certain tradeoffs between battery life, or in the instance of implantable medical devices with non-rechargeable batteries, between device replacement, and the resolution, sampling frequency, or storage of sensed physiologic information.

Physiologic information, such as indicative of a potential medical device event, can be used to transition from a low-power monitoring mode (e.g., a low-power mode) to a higher-power or higher-resolution monitoring mode (e.g., a high-power mode). In certain examples, the low-power mode can include a low resource mode, characterized as requiring less power, processing time, memory, or communication time or bandwidth (e.g., transferring less data, etc.) than a corresponding high-power mode. The high-power mode can include a relatively higher resource mode, characterized as requiring more power, processing time, memory, or communication time or bandwidth than the corresponding low-power mode.

Traditional syncope detection uses patient heart rate or blood pressure information as indicative of a potential syncope event, including capturing physiologic information detected in the low-power monitoring mode and currently residing in a loop recorder, in long-term storage. However, such information in the loop recorder was sensed in the low-power mode, often having a lower sampling frequency, lower sampling resolution, or a different set of sensed information or sensed parameters. In certain examples, the earlier indication provided by the patient heart sound information, or specific illustrated heart sound parameters, can enable higher resolution sampling of relevant patient physiologic information leading up to and including a syncope or potential syncope event that previously did not exist without always sampling in the higher-power or higher-resolution mode, or with additional sensors, unnecessarily reducing medical device life span, wasting power and storage resources. This is different than choosing to store information from a loop recorder alone (although this can enable earlier triggering of storage from the loop recorder into long-term storage).

The change in patient modes can enable higher resolution sampling or an increase in the sampling frequency or number or types of sensors used to sense physiologic information leading up to and including the syncope or potential syncope event, that may cover the transition that would previously have triggered the high-power mode that would otherwise be lost. For example, an early detection of a potential syncope event can trigger the high-power mode in one or more cardiac electrical sensors (e.g., electrocardiogram (EGM), heart rate, etc.), cardiac acceleration sensors (e.g., accelerometer information indicative of heart sounds, cardiac wall motion, etc.), or other sensors that otherwise may not be available in the low-power mode, etc.

For example, heart sounds and patient activity are often detected using non-overlapping time periods of the same, single- or multi-axis accelerometer, at different sampling frequencies and power costs. In one example, the transition to a high-power mode can include using the accelerometer to detect heart sounds throughout the high-power mode, or at a larger percentage of the high-power mode than during a corresponding low-power mode, etc.

In contrast to the patient blood pressure and heart rate information in FIG. 1, the S2 information 108 sharply dips from a baseline (e.g., about 85 mG) after time 0 minutes, at the first time 103, for the first several seconds (e.g., to about 55 mG at about 10 seconds) before sharply rising to an elevated level (e.g., to about 100 mG at about 30 seconds) where it remains elevated until starting to decline after between 2 and 3 minutes at a third position 109, with a noticeable step decrease before 3 minutes, then another sharp decrease and fall before 5 minutes, dropping until the tilt table test end at time 8 minutes, at the second time 104 (e.g., reaching about 45 mG at time 8 minutes), and continuing to drop shortly thereafter before sharply rising to an even more elevated level than shown during the tilt table test (e.g., to approximately 130 mG at time 9 minutes).

The S1 information 110 shows an extraordinary rise from a baseline (e.g., about 65 mG) after time 0 minutes, at the first time 103, for the first several seconds to an elevated level (e.g., to about 150 mG at about 20 seconds, more than doubling) at a fourth position 111, where it remains elevated until starting to decline between 2 and 3 minutes at a fifth position 112, with a noticeable step decrease before 3 minutes, then another sharp decrease before 5 minutes, before more sharply decreasing until the tilt table test end at time 8 minutes, at the second time 104 (e.g., reaching about 65 mG at time 8 minutes), and continuing to drop shortly thereafter before rising then falling back to the baseline.

The present inventors have recognized, among other things, that a coordinated decrease in both S1 and S2 amplitude can be indicative of an approaching syncope event. In certain examples, an assessment circuit can determine one or more parameters, during a tilt table test, to detect a syncope response before the traditional combination of heart rate and blood pressure or heart rate alone, and end the test before the patient blood pressure begins to drop and the patient loses consciousness.

In clinical settings, patient blood pressure can be detected using a wearable cuff. In ambulatory, non-clinical settings, patient blood pressure can be measured using a cuff by the patient or another caregiver, or by an implanted, invasive blood pressure sensor. Detecting a syncope event using heart sound information can provide additional functionality to an existing system without an implantable blood pressure sensor, or provide ambulatory functionality not otherwise capable by an external blood pressure cuff.

Although illustrated as a tilt table test in FIG. 1, the patient response can be detected in similar real-world high risk conditions, such as during patient posture changes (e.g., from laying down to sitting or standing, from sitting to standing, etc.), detected inactive upright periods (e.g., standing with patient activity below a walking threshold, indicating that the patient is standing still, etc.), etc. In an example, patient position or physical activity can be detected, such as using an accelerometer or position sensor, etc. In response to the detected high risk conditions, such as described above, patient heart sound information can be used to transition device behavior, such as to trigger storage of patient information (e.g., from a loop recorder to long-term or non-volatile memory), to alter one or more patient monitoring modes, etc. In certain examples, patient heart sound information in combination with patient heart rate information can be used to provide a differential diagnosis of a detected or recorded syncope event, or to provide an alert or trigger a therapy to the patient.

Figure 2:
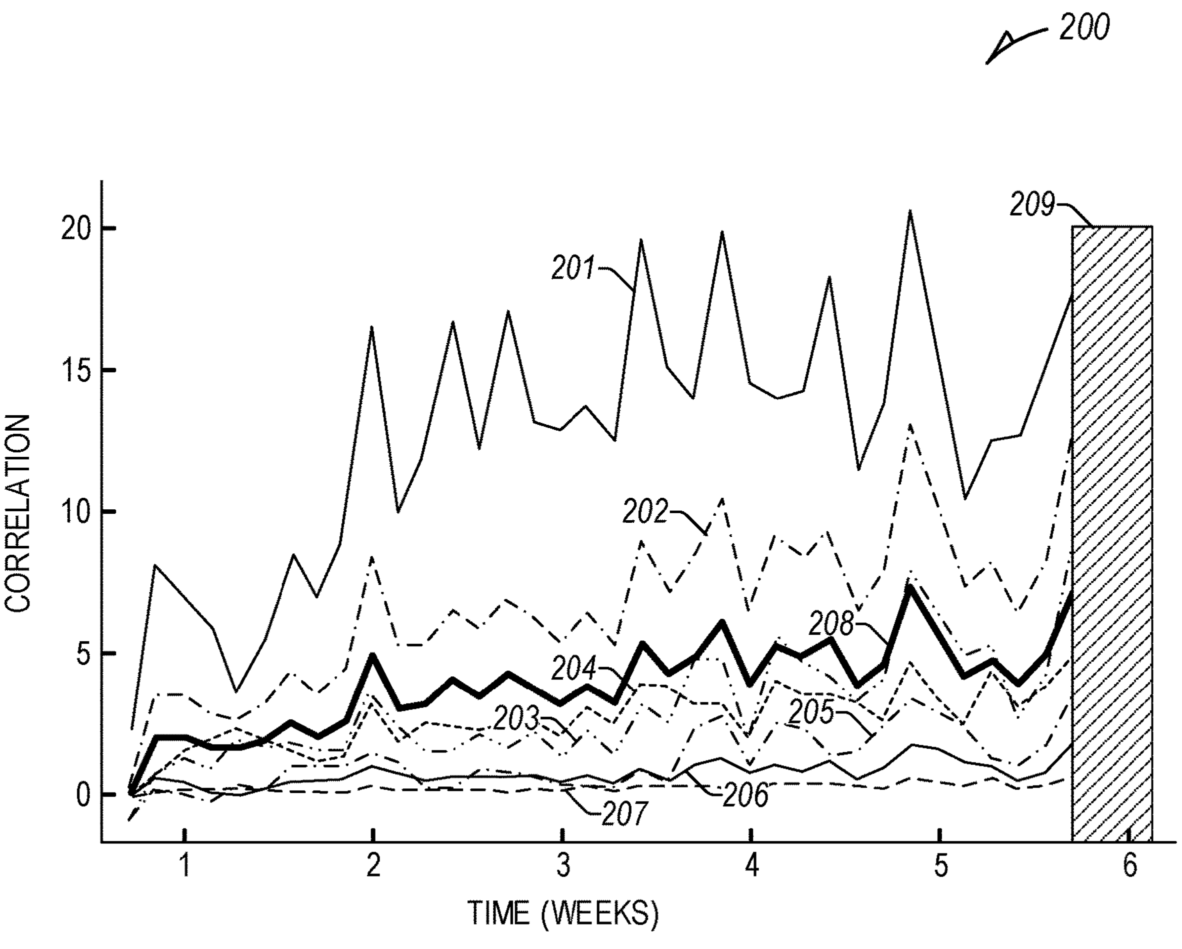
FIG. 2 illustrates a relationship between different heart sound parameters in the weeks leading up to a syncope event.

FIG. 2 illustrates a relationship 200 between different combinations of heart sound parameters for a patient in the weeks leading up to a syncope event and ensuing hospitalization at 209, indicating that certain parameters or combinations of different heart sound parameters (e.g., combinations of heart sound amplitude values) are predictive of a syncope event or potential syncope event.

The different combinations of heart sound parameters include first through eighth composite parameters 201-207, and can be described as the:

$$\text{first composite parameter } \mathbf{201} \propto S1/(S2 \times S3 \times S4) \quad (1)$$

$$\text{second composite parameter } \mathbf{202} \propto S1/(S2 \times S3) \quad (2)$$

$$\text{third composite parameter } \mathbf{203} \propto (S1 \times S4)/(S2 \times S3) \quad (3)$$

$$\text{fourth composite parameter } \mathbf{204} \propto S4/(S2 \times S3) \quad (4)$$

$$\text{fifth composite parameter } \mathbf{205} \propto S1/S2 \quad (5)$$

$$\text{sixth composite parameter } \mathbf{206} \propto S1/S3 \quad (6)$$

$$\text{seventh composite parameter } \mathbf{207} \propto S4/S3 \quad (7)$$

$$\text{eighth composite parameter } 208 \propto \sum_1^n \frac{\text{parameters}}{n} \quad (8)$$

The eighth composite parameter 208 can be the average of the first through seventh parameters 201-207.

Although not illustrated in FIG. 2, after the syncope event 209, the first composite parameter 201 falls more than the other parameters. The delta difference before and after the event of the first composite parameter 201 is greater than the other composite parameters. The second composite parameter 202 reverts to the average after the syncope event 209. The third composite parameter 203 remains most elevated after the syncope event 209. The relative differences between parameters before and after the syncope event 209 can be indicative of a risk level of a possible syncope event. For example, the first or second composite parameters 201, 202 exceeding the eighth composite parameter 208 (the average composite parameter) can be predictive or indicative of a high risk of a future syncope event, with the amount the that the first or second composite parameters 201, 202 exceed the eighth composite parameter 208 correlative to a higher level of risk (e.g., the more the first or second composite parameters 201, 202 exceed the eighth composite parameter 208, the greater the risk, etc.). In contrast, the third composite parameter 203 exceeding the eighth composite parameter 208, in certain examples in combination with the first or second composite parameters 201, 202 near or below the eight composite parameter 208, can be predictive or indicative of a low risk of a future syncope event, with the amount that the third composite parameter 203 exceeds the eighth composite parameter 208 correlative to a lower level of risk (e.g., the more the third composite parameter 203 exceeds the eight composite parameter 208, the lower the risk, etc.).

In other examples, other heart sound information can be used to detect a syncope event, or a risk of a future syncope event, including: a change in short term, daily, or real-time heart sound information, such as a change in S1 or S2 amplitude.

In other examples, although not illustrated in the figures, other physiologic information can be combined with the heart sound information or one or more heart sound parameters to detect a syncope event, including, among others, one or more of: a change in patient heart rate, a change in patient heart rate variability, a change in patient posture, a detected stationary posture (e.g., standing) for a period of time without movement or activity, a blood level trigger (e.g., a reduction in oxygen saturation, such as detected using a photoplethysmography (PPG) sensor, or a change or increase in patient $CO_2$ level, etc.), an increase in patient temperature (e.g., leading up to an event for detection, or following a potential event for confirmation, etc.), a change in patient altitude (e.g., detected using an altimeter, indicative of a change in position, etc.), a patient-initiated trigger (e.g., recent consumption of prescribed medication that might cause vasodilation, etc.), detection of parasympathetic activity (e.g., indicative of parasympathetic overdrive, etc.), etc.

In an example, a heart sound parameter, such as one or more of the first or second composite parameters 201, 202, exceeding a relative threshold, or a change in a heart sound parameter exceeding a relative threshold over a period of time (e.g., a percentage increase from a baseline over a number of days, weeks, etc.) can be used to change one or more device parameters, transition a medical device from a low-power to a high-power mode, provide one or more alerts to the patient or a clinician, or provide one or more therapies (e.g., pacing therapies, drug therapies, etc.), such as otherwise described herein.

Figure 3:
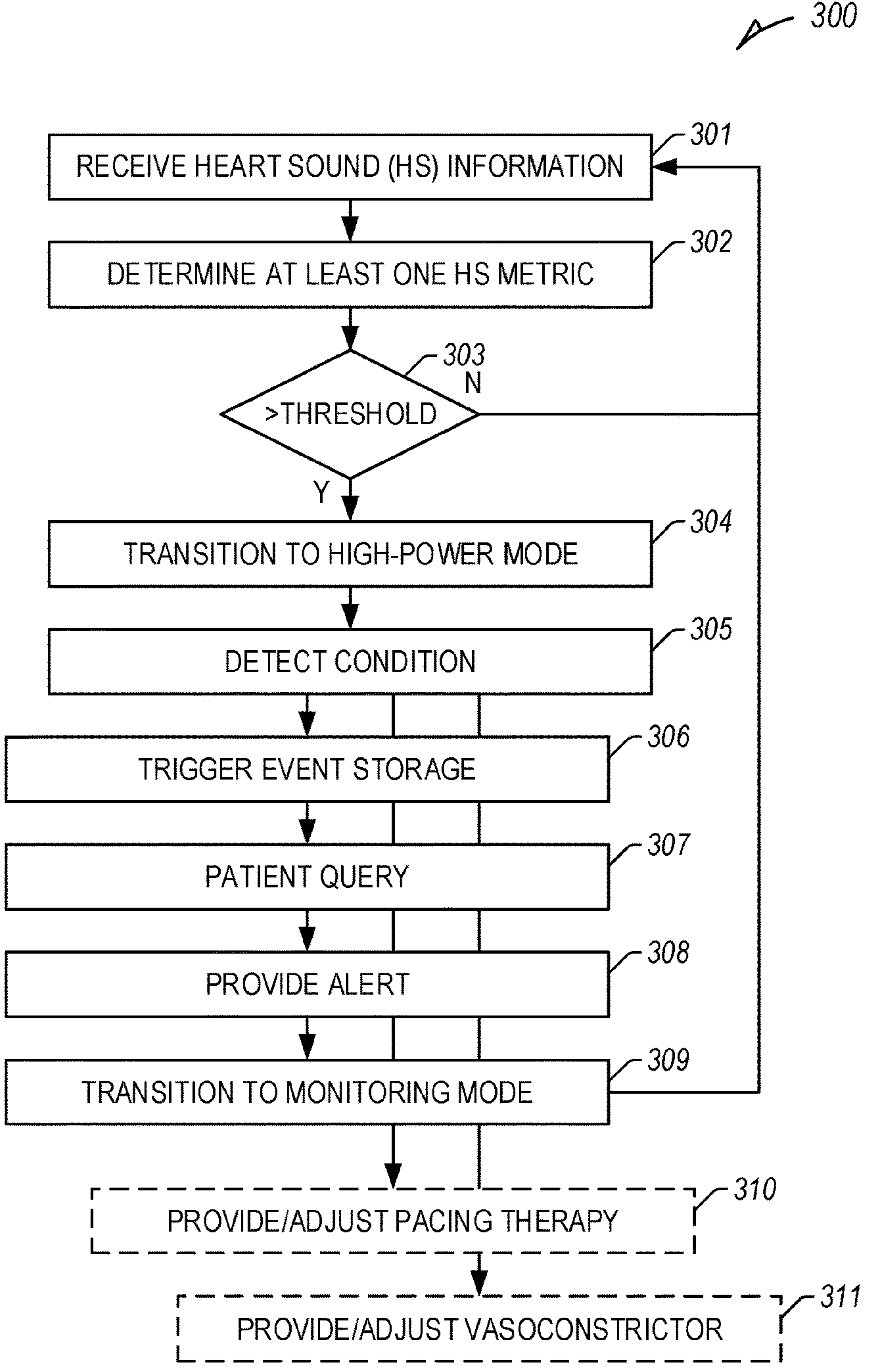
FIG. 3 illustrates an example method of detecting syncope using heart sound information.

FIG. 3 illustrates an example method 300 of detecting a potential syncope event using heart sound information, such as using an assessment circuit of a medical device (e.g., an implantable medical device, an ambulatory medical device, etc.), and to control or otherwise alter a function of a medical device in response to the detected potential syncope event, such as to transition a behavior or mode of operation of the medical device from a first low-power mode to a second high-power mode.

At 301, heart sound information can be received, such as using a signal receiver circuit of the medical device, from a heart sound sensor (e.g., an accelerometer, etc.) or heart sound sensor circuit. In certain examples, additional physiologic information can be received, such as one or more of cardiac electrical information (e.g., heart rate information, etc.), activity information of the patient, or posture information of the patient, from one or more other sensor or sensor circuits.

At 302, at least one heart sound parameter or composite parameter can be determined or received, such as using an assessment circuit. In an example, the heart sound parameter can include one or more of an S1, S2, S3, or S4 value, such as an amplitude or energy value (e.g., an energy value in a heart sound window defined by, among other things, a cardiac signal feature, one or more other heart sounds, or combinations thereof, over one or more cardiac cycles, etc.). In an example, a heart sound parameter can include information of or about multiple of the same heart sound parameter or different combinations of heart sound parameters over one or more cardiac cycles or a specified time period (e.g., 1 minute, 1 hour, 1 day, 1 week, etc.). For example, a heart sound parameter can include a composite S1 parameter representative of a plurality of S1 parameters, for example, over a certain time period (e.g., a number of cardiac cycles, a representative time period, etc.).

In an example, the heart sound parameter can include an ensemble average of a particular heart sound over a heart sound waveform, such as that disclosed in the commonly assigned Siejko et al. U.S. Pat. No. 7,115,096 entitled "THIRD HEART SOUND ACTIVITY INDEX FOR HEART FAILURE MONITORING," or in the commonly assigned Patangay et al. U.S. Pat. No. 7,853,327 entitled "HEART SOUND TRACKING SYSTEM AND METHOD," each of which are hereby incorporated by reference in their entireties, including their disclosures of ensemble averaging an acoustic signal and determining a particular heart sound of a heart sound waveform. In other examples, the signal receiver circuit can receive the at least one heart sound parameter or composite parameter, such as from a heart sound sensor or a heart sound sensor circuit.

At 303, the determined heart sound parameter or composite parameter can be compared to one or more thresholds. In an example, the one or more thresholds, parameters, or orders of parameters can be relative parameters, such as relative to a baseline value, consistent with the information illustrated in FIGS. 1 and 2 leading up to the syncope or potential syncope event. For example, FIG. 1 illustrates a substantial rise in S1 amplitude, greater than 200%. In an example, a relative S1 threshold can be 100% above the baseline S1 amplitude or greater (e.g., 150%, 200%, etc.). In other examples, one or more other relative or absolute values can be used, such as an increase above 50 mG, etc. A similar threshold can be used with respect to S2 amplitude or heart rate, or a combination of one or more thresholds, combined in a single metric or separately exceeding respective thresholds, for example, consistent with or similar to the time periods, relative or absolute values (e.g., increases or decreases, etc.), or other signatures of the respective physiologic information.

At 303, if the determined heart sound parameter or composite parameter exceeds a threshold, indicative of a potential syncope event, a behavior or mode of operation of the medical device can be transitioned at 304, such as from a low-power mode to a high-power mode. In certain examples, the high-power mode can be in contrast to the low-power mode, and can include one or more of: enabling one or more additional sensors, transitioning from a low-power sensor or set of sensors to a higher-power sensor or set of sensors, triggering additional sensing from one or more additional sensors or medical devices, increasing a sensing frequency or a sensing or storage resolution, increasing an amount of data to be collected, communicated (e.g., from a first medical device to a second medical device, etc.), or stored, triggering storage of currently available information from a loop recorder in long-term storage or increasing the storage capacity or time period of a loop recorder, or otherwise altering device behavior to capture additional or higher-resolution physiologic information or perform more processing, etc.

In an example, the transition to the high-power mode at 304, or the comparison of the determined heart sound parameter or composite parameter to the threshold, can be further in response to a detected high risk syncope position of the patient, such as a change in patient posture (e.g., from laying down to sitting or standing, from sitting to standing, etc.) or an inactive upright period (e.g., standing with patient activity below a walking threshold, indicating that the patient is standing still, etc.).

In an example, the determined heart sound metric or composite parameter can include an increase in S1 amplitude in a relatively short time period, in certain examples, overlapping with or occurring in response to a detected high risk syncope position of the patient. In an example, as illustrated in FIG. 1, the relatively short time period can be less than one minute, in certain examples, less than 30 seconds, less than 15 seconds, etc. In other examples, the composite parameter can include a combination of an increase in patient heart rate and S1 amplitude, or one or more other heart sound parameters, in the relatively short time period overlapping with or occurring in response to the detected high risk syncope position of the patient. In an example, both heart sound and cardiac electrical information must separately exceed one or more thresholds to indicate the potential syncope event and transition the behavior or mode of operation of the medical device.

At 305, a condition, such as an indication of a syncope event (e.g., an NMS event), can be detected, confirmed, or presented for confirmation, such as using the assessment circuit and information from the high-power mode or the heart sound information received at 301 or other received physiologic information. For example, an atypical decrease in S2, such as illustrated in FIG. 1, can be indicative of a syncope event, such as a VVS event, etc. In certain examples, the atypical decrease in S2 greater than a threshold, such as relative reduction (e.g., a 20% reduction, etc.) over a period of several minutes, etc., can be indicative of a potential syncope event. In an example, the atypical decrease in S2, augmented by similar changes in HR and S1 greater than respective thresholds at respective times, such as illustrated in FIG. 1 (e.g., a corresponding atypical decrease in S2, a corresponding rise in FIR, or a subsequent fall in HR after the detected decrease in S2, etc.), can be used to augment detection (e.g., increase the likelihood) of the potential syncope event.

Additionally, or alternatively, event storage can be triggered at 306, such as in response to the detected condition at 305 or the determined heart sound parameter or composite parameter exceeding the threshold at 303. Information sensed or recorded in the high-power mode can be transitioned from short-term storage, such as in a loop recorder, to long-term or non-volatile memory, or in certain examples, prepared for communication to an external device separate from the medical device. In an example, heart sound information and heart rate information leading up to and in certain examples including the detected condition can be stored, such as to increase the specificity of detection, but also to possibly provide information to a clinician or caregiver to determine the source of the syncope event, or to distinguish between different types of syncope events. In an example, multiple loop recorder windows (e.g., 2-minute windows) can be stored sequentially, starting sooner than previously stored using detecting syncope events using cardiac electrical information (e.g., HR, electrocardiogram (EGM), etc.). In systems without this early detection, to record this information, a loop recorder with a longer time period would be required at substantial additional cost (e.g., power, processing resources, component cost, amount of memory, etc.). Storing multiple windows using this early detection leading up to a single event can provide full event assessment with power and cost savings, in contrast to the longer loop recorder windows. In addition, the early detection can trigger additional parameter computation or storage, at different resolution or sampling frequency, without unduly taxing finite system resources.

At 307, the medical device can trigger a patient query associated with the detected condition. In certain examples, the patient query can be provided to a patient device having user voice or text input capabilities, such as a smart watch, a cellular or smart phone, a computer, etc. Questions about the symptoms leading up to and including the detected event, prior to pushing any event information to physicians, can be stored with the detected event. Information from the patient about the detected condition can be received from the patient in response to the triggered patient query, including confirmation of actual syncope events, etc.

At 308, an alert can be provided, such as to the patient, to a clinician, or to one or more other caregivers (e.g., using a patient smart watch, a cellular or smart phone, a computer, etc.), such as in response to the transition to the high-power mode or in response to the detected condition or receiving information in response the triggered patient query. In other examples, the medical device itself can beep or vibrate to warn the patient of the detected condition. For example, the patient can be alerted in response to a detected condition so they can engage in corrective action, such as sitting down, etc. Alternatively, the medical device can emit a sound or vibration to notify the patient that a syncope event is likely to occur. At 309, the medical device can transition from the high-power mode to the low-power mode.

In certain examples, a therapy can be provided in response to the detected condition. For example, at 310, a pacing therapy (e.g., DDD pacing) can be provided, enabled, or adjusted, such as to reduce syncope due to a reduction in heart rate, ventricular filling, or blood pressure associated with a syncope event, for example, such as disclosed in the commonly assigned Sanders U.S. Pat. No. 8,761,878 entitled "IMPLANTABLE CARDIAC MONITOR UPGRADEABLE TO PACEMAKER OR CARDIAC RESYNCHRONIZATION DEVICE," or in the commonly assigned Spinelli et al. U.S. Pat. No. 8,498,703 entitled "METHOD AND SYSTEM FOR TREATMENT OF NEUROCARDIOGENIC SYNCOPE," each of which are hereby incorporated by reference in their entireties, including their disclosure of providing a pacing therapy or pacing pulses to alleviate or at least partially avoid syncope.

At 311, a vasoconstrictor (e.g., pressor drugs, etc.) can be triggered, provided, or adjusted, such as using a drug pump, in response to the detected condition, to contract or constrict the blood vessels, counteracting hypotension, a pooling of blood in the extremities, or a lack of blood supply to the brain, such as to alleviate or at least partially avoid syncope. In other examples, application of a vasoconstrictor can be triggered in response to the detected condition, alone or in combination with a pacing therapy, such as that described above, such as to both increase arterial pressure and to maintain cardiac output.

In an example, the assessment circuit can detect or receive indications of actual syncope events, such as from medical records, patient or clinician input, detected falls after detected indications of syncope, or other confirmations of actual syncope events, etc., and determine a correlation between detected indications of syncope and confirmed syncope events. Additionally, signal response leading up to a syncope event, such as those illustrated in FIGS. 1 and 2, can be correlated to interventions, such as those taken in response to an alert of a detected indication of a potential syncope event and patient activity taken in response to the provided alert, in certain examples, confirmed by patient feedback triggered following the alert. If the correlation between detected indications of potential syncope events and confirmed syncope events becomes weaker over time, the patient may be experiencing a lower likelihood of syncope, or the attempted interventions (e.g., drug therapy, pacing therapy, triggered patient activities, etc.) can be working to reduce the occurrence of syncope events.

Figure 4:
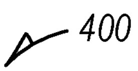
FIG. 4 illustrates an example system to detect syncope using heart sound information.
Figure 4:
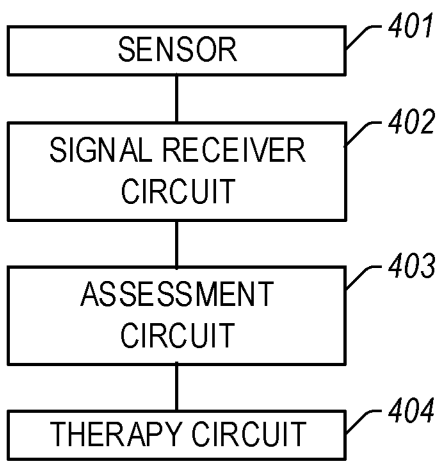

FIG. 4 illustrates an example system 400 to detect syncope using heart sound information. The example system 400 can include a medical-device system, a cardiac rhythm management (CRM) device, etc. In an example, one or more aspects of the example system 400 can be a component of, or communicatively coupled to, an ambulatory medical device (AMD), an insertable cardiac monitor, etc. The system 400 can be configured to monitor, detect, or treat various physiologic conditions of the body, such as cardiac conditions associated with a reduced ability of a heart to sufficiently deliver blood to a body, including heart failure, arrhythmias, dyssynchrony, etc., or one or more other physiologic conditions and, in certain examples, can be configured to provide electrical stimulation or one or more other therapies or treatments to the patient.

The system 400 can include a single medical device or a plurality of medical devices implanted in a patient's body or otherwise positioned on or about the patient to monitor patient physiologic information of the patient using one or more sensors, such as a sensor 401. In an example, the sensor 401 can include one or more of: a respiration sensor configured to receive respiration information (e.g., a respiration rate, a respiration volume (tidal volume), etc.); an acceleration sensor (e.g., an accelerometer, a microphone, etc.) configured to receive cardiac acceleration information (e.g., cardiac vibration information, pressure waveform information, heart sound information, endocardial acceleration information, acceleration information, activity information, posture information, etc.); an impedance sensor (e.g., intrathoracic impedance sensor, transthoracic impedance sensor, etc.) configured to receive impedance information, a cardiac sensor configured to receive cardiac electrical information; an activity sensor configured to receive information about a physical motion (e.g., activity, steps, etc.); a posture sensor configured to receive posture or position information; a pressure sensor configured to receive pressure information; a plethysmograph sensor (e.g., a photoplethysmography sensor, etc.); a chemical sensor (e.g., an electrolyte sensor, a pH sensor, an anion gap sensor, etc.); a temperature sensor; a skin elasticity sensor, or one or more other sensors configured to receive physiologic information of the patient.

The example system 400 can include a signal receiver circuit 402 and an assessment circuit 403. The signal receiver circuit 402 can be configured to receive physiologic information of a patient (or group of patients) from the sensor 401. The assessment circuit 403 can be configured to receive information from the signal receiver circuit 402, and to determine one or more parameters (e.g., physiologic parameters, stratifiers, etc.) or existing or changed patient conditions (e.g., indications of patient dehydration, respiratory condition, cardiac condition (e.g., heart failure, arrhythmia), sleep disordered breathing, etc.) using the received physiologic information, such as described herein. The physiologic information can include, among other things, cardiac electrical information, impedance information, respiration information, heart sound information, activity information, posture information, temperature information, or one or more other types of physiologic information.

The assessment circuit 403 can be configured to provide an output to a user, such as to a display or one or more other user interface, the output including a score, a trend, an alert, or other indication. In other examples, the assessment circuit 403 can be configured to provide an output to another circuit, machine, or process, such as a therapy circuit 404 (e.g., a cardiac resynchronization therapy (CRT) circuit, a chemical therapy circuit, etc.), etc., to control, adjust, or cease a therapy of a medical device, a drug delivery system, etc., or otherwise alter one or more processes or functions of one or more other aspects of a medical-device system, such as one or more cardiac resynchronization therapy parameters, drug delivery, dosage determinations or recommendations, etc. In an example, the therapy circuit 404 can include one or more of a stimulation control circuit, a cardiac stimulation circuit, a neural stimulation circuit, a dosage determination or control circuit, etc. In other examples, the therapy circuit 404 can be controlled by the assessment circuit 403, or one or more other circuits, etc.

Traditional cardiac rhythm management devices, such as insertable cardiac monitors, pacemakers, defibrillators, or cardiac resynchronizers, include implantable or subcutaneous devices having hermetically sealed housings configured to be implanted in a chest of a patient. The cardiac rhythm management device can include one or more leads to position one or more electrodes or other sensors at various locations in or near the heart, such as in one or more of the atria or ventricles of a heart, etc. Accordingly, cardiac rhythm management devices can include aspects located subcutaneously, though proximate the distal skin of the patient, as well as aspects, such as leads or electrodes, located near one or more organs of the patient. Separate from, or in addition to, the one or more electrodes or other sensors of the leads, the cardiac rhythm management device can include one or more electrodes or other sensors (e.g., a pressure sensor, an accelerometer, a gyroscope, a microphone, etc.) powered by a power source in the cardiac rhythm management device. The one or more electrodes or other sensors of the leads, the cardiac rhythm management device, or a combination thereof, can be configured detect physiologic information from the patient, or provide one or more therapies or stimulation to the patient.

Implantable devices can additionally or separately include leadless cardiac pacemakers (LCPs), small (e.g., smaller than traditional implantable cardiac rhythm management devices, in certain examples having a volume of about 1 cc, etc.), self-contained devices including one or more sensors, circuits, or electrodes configured to monitor physiologic information (e.g., heart rate, etc.) from, detect physiologic conditions (e.g., tachycardia) associated with, or provide one or more therapies or stimulation to the heart without traditional lead or implantable cardiac rhythm management device complications (e.g., required incision and pocket, complications associated with lead placement, breakage, or migration, etc.). In certain examples, an leadless cardiac pacemakers can have more limited power and processing capabilities than a traditional cardiac rhythm management device; however, multiple leadless cardiac pacemakers can be implanted in or about the heart to detect physiologic information from, or provide one or more therapies or stimulation to, one or more chambers of the heart. The multiple leadless cardiac pacemaker can communicate between themselves, or one or more other implanted or external devices.

Figure 5:
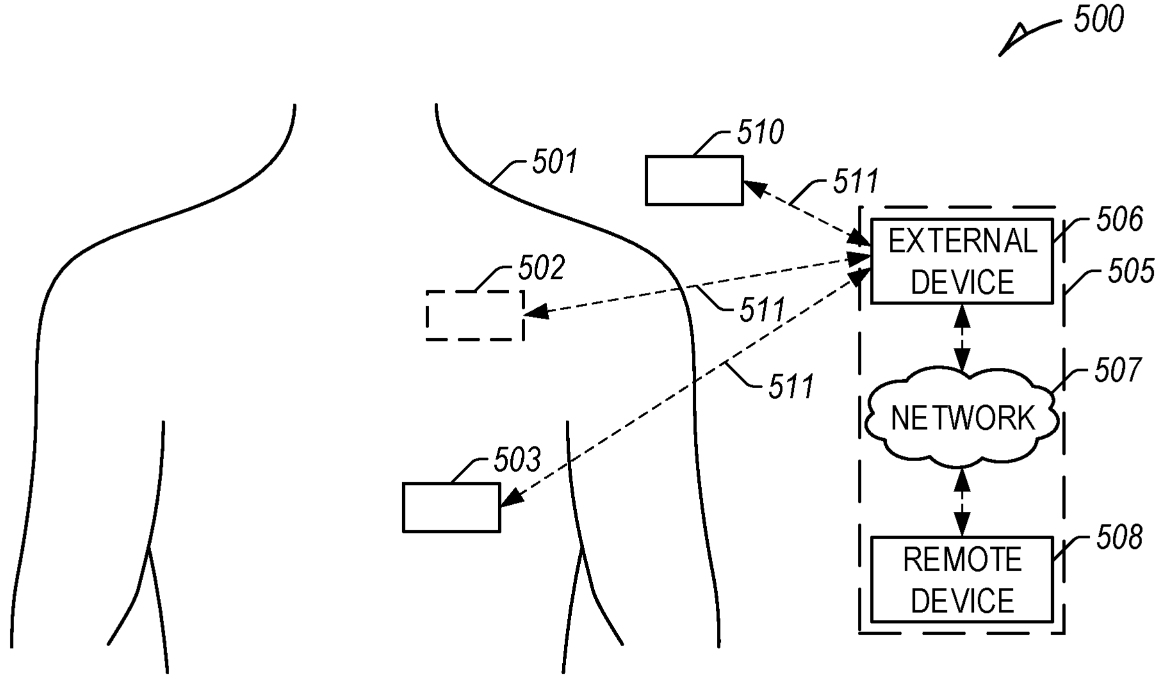
FIG. 5 illustrates an example patient management system and portions of an environment in which the system may operate.

FIG. 5 illustrates an example patient management system 500 and portions of an environment in which the patient management system 500 may operate. The patient management system 500 can perform a range of activities, including remote patient monitoring and diagnosis of a disease condition. Such activities can be performed proximal to a patient 501, such as in a patient home or office, through a centralized server, such as in a hospital, clinic, or physician office, or through a remote workstation, such as a secure wireless mobile computing device.

The patient management system 500 can include one or more ambulatory medical devices, an external system 505, and a communication link 511 providing for communication between the one or more ambulatory medical devices and the external system 505. The one or more ambulatory medical devices can include an implantable medical device (IMD) 502, a wearable medical device 503, or one or more other implantable, leadless, subcutaneous, external, wearable, or ambulatory medical devices configured to monitor, sense, or detect information from, determine physiologic information about, or provide one or more therapies to treat various conditions of the patient 501, such as one or more cardiac or non-cardiac conditions (e.g., dehydration, sleep disordered breathing, etc.).

In an example, the implantable medical device 502 can include one or more traditional cardiac rhythm management devices implanted in a chest of a patient, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the patient 501. In another example, the implantable medical device 502 can include a monitor implanted, for example, subcutaneously in the chest of patient 501, the implantable medical device 502 including a housing containing circuitry and, in certain examples, one or more sensors, such as a temperature sensor, etc.

The implantable medical device 502 can include an assessment circuit configured to detect or determine specific physiologic information of the patient 501, or to determine one or more conditions or provide information or an alert to a user, such as the patient 501 (e.g., a patient), a clinician, or one or more other caregivers or processes, such as described herein. The implantable medical device 502 can alternatively or additionally be configured as a therapeutic device configured to treat one or more medical conditions of the patient 501. The therapy can be delivered to the patient 501 via the lead system and associated electrodes or using one or more other delivery mechanisms. The therapy can include delivery of one or more drugs to the patient 501, such as using the implantable medical device 502 or one or more of the other ambulatory medical devices, etc. In some examples, therapy can include cardiac resynchronization therapy for rectifying dyssynchrony and improving cardiac function in heart failure patients. In other examples, the implantable medical device 502 can include a drug delivery system, such as a drug infusion pump to deliver drugs to the patient for managing arrhythmias or complications from arrhythmias, hypertension, hypotension, or one or more other physiologic conditions. In other examples, the implantable medical device 502 can include one or more electrodes configured to stimulate the nervous system of the patient or to provide stimulation to the muscles of the patient airway, etc.

The wearable medical device 503 can include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.).

The external system 505 can include a dedicated hardware/software system, such as a programmer, a remote server-based patient management system, or alternatively a system defined predominantly by software running on a standard personal computer. The external system 505 can manage the patient 501 through the implantable medical device 502 or one or more other ambulatory medical devices connected to the external system 505 via a communication link 511. In other examples, the implantable medical device 502 can be connected to the wearable medical device 503, or the wearable medical device 503 can be connected to the external system 505, via the communication link 511. This can include, for example, programming the implantable medical device 502 to perform one or more of acquiring physiologic data, performing at least one self-diagnostic test (such as for a device operational status), analyzing the physiologic data, or optionally delivering or adjusting a therapy for the patient 501. Additionally, the external system 505 can send information to, or receive information from, the implantable medical device 502 or the wearable medical device 503 via the communication link 511. Examples of the information can include real-time or stored physiologic data from the patient 501, diagnostic data, such as detection of patient hydration status, hospitalizations, responses to therapies delivered to the patient 501, or device operational status of the implantable medical device 502 or the wearable medical device 503 (e.g., battery status, lead impedance, etc.). The communication link 511 can be an inductive telemetry link, a capacitive telemetry link, or a radio-frequency (RF) telemetry link, or wireless telemetry based on, for example, "strong" Bluetooth or IEEE 602.11 wireless fidelity "Wi-Fi" interfacing standards. Other configurations and combinations of patient data source interfacing are possible.

The external system 505 can include an external device 506 in proximity of the one or more ambulatory medical devices, and a remote device 508 in a location relatively distant from the one or more ambulatory medical devices, in communication with the external device 506 via a communication network 507. Examples of the external device 506 can include a medical device programmer. The remote device 508 can be configured to evaluate collected patient or patient information and provide alert notifications, among other possible functions. In an example, the remote device 508 can include a centralized server acting as a central hub for collected data storage and analysis. The server can be configured as a uni-, multi-, or distributed computing and processing system. The remote device 508 can receive data from multiple patients. The data can be collected by the one or more ambulatory medical devices, among other data acquisition sensors or devices associated with the patient 501. The server can include a memory device to store the data in a patient database. The server can include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more ambulatory medical devices, such as the implantable medical device. By way of example, alert notifications can include a Web page update, phone or pager call, E-mail, SMS, text or "Instant" message, as well as a message to the patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiologic data associated with the detected medical event to physiologic data associated with the historical alerts.

The remote device 508 may additionally include one or more locally configured clients or remote clients securely connected over the communication network 507 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 508, including the server and the interconnected clients, may also execute a follow-up scheme by sending follow-up requests to the one or more ambulatory medical devices, or by sending a message or other communication to the patient 501 (e.g., the patient), clinician or authorized third party as a compliance notification.

The communication network 507 can provide wired or wireless interconnectivity. In an example, the communication network 507 can be based on the Transmission Control Protocol/Internet Protocol (TCP/IP) network communication specification, although other types or combinations of networking implementations are possible. Similarly, other network topologies and arrangements are possible.

One or more of the external device 506 or the remote device 508 can output the detected medical events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 506 or the remote device 508 can include a respective display unit for displaying the physiologic or functional signals, or alerts, alarms, emergency calls, or other forms of warnings to signal the detection of arrhythmias. In some examples, the external system 505 can include an external data processor configured to analyze the physiologic or functional signals received by the one or more ambulatory medical devices, and to confirm or reject the detection of arrhythmias. Computationally intensive algorithms, such as machine-learning algorithms, can be implemented in the external data processor to process the data retrospectively to detect cardia arrhythmias.

Portions of the one or more ambulatory medical devices or the external system 505 can be implemented using hardware, software, firmware, or combinations thereof. Portions of the one or more ambulatory medical devices or the external system 505 can be implemented using an application-specific circuit that can be constructed or configured to perform one or more functions or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" can include electronic circuits configured to receive information and provide an electronic output representative of such received information.

The therapy device 510 can be configured to send information to or receive information from one or more of the ambulatory medical devices or the external system 505 using the communication link 511. In an example, the one or more ambulatory medical devices, the external device 506, or the remote device 508 can be configured to control one or more parameters of the therapy device 510. The external system 505 can allow for programming the one or more ambulatory medical devices and can receives information about one or more signals acquired by the one or more ambulatory medical devices, such as can be received via a communication link 511. The external system 505 can include a local external implantable medical device programmer. The external system 505 can include a remote patient management system that can monitor patient status or adjust one or more therapies such as from a remote location.

Figure 6:
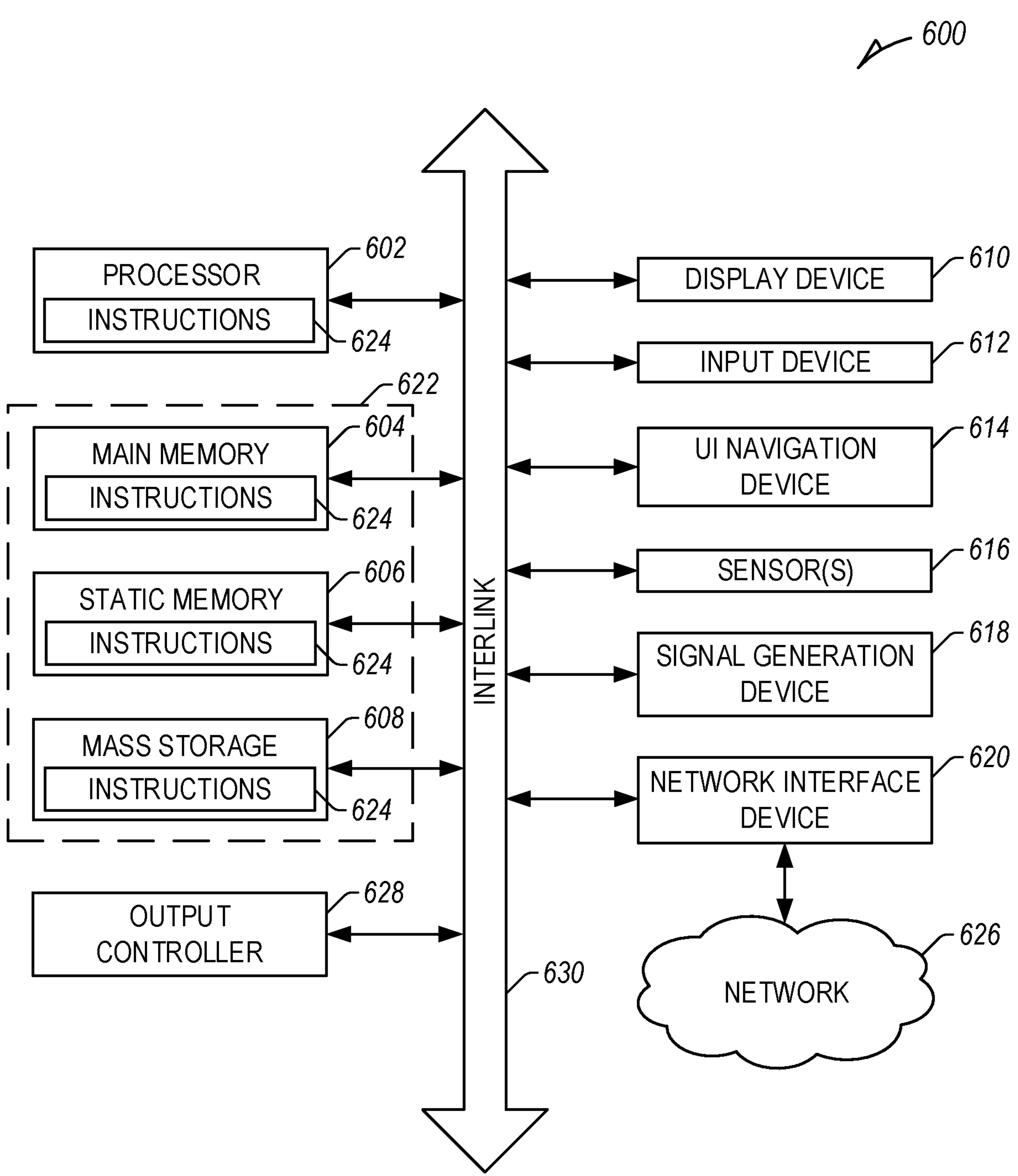
FIG. 6 illustrates a block diagram of an example machine upon which any one or more of the techniques discussed herein may perform.

FIG. 6 illustrates a block diagram of an example machine 600 upon which any one or more of the techniques (e.g., methodologies) discussed herein may perform. Portions of this description may apply to the computing framework of one or more of the medical devices described herein, such as the implantable medical device, the external programmer, etc. Further, as described herein with respect to medical device components, systems, or machines, such may require regulatory-compliance not capable by generic computers, components, or machinery.

Examples, as described herein, may include, or may operate by, logic or a number of components, or mechanisms in the machine 600. Circuitry (e.g., processing circuitry, an assessment circuit, etc.) is a collection of circuits implemented in tangible entities of the machine 600 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 600 follow.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 600 may include a hardware processor 602 (e.g., a central processing unit (CPU), a graphics processing unit (GPU), a hardware processor core, or any combination thereof), a main memory 604, a static memory (e.g., memory or storage for firmware, microcode, a basic-input-output (BIOS), unified extensible firmware interface (UEFI), etc.) 606, and mass storage 608 (e.g., hard drive, tape drive, flash storage, or other block devices) some or all of which may communicate with each other via an interlink (e.g., bus) 630. The machine 600 may further include a display unit 610, an input device 612 (e.g., a keyboard), and a user interface (UI) navigation device 614 (e.g., a mouse). In an example, the display unit 610, input device 612, and UI navigation device 614 may be a touch screen display. The machine 600 may additionally include a signal generation device 618 (e.g., a speaker), a network interface device 620, and one or more sensors 616, such as a global positioning system (GPS) sensor, compass, accelerometer, or one or more other sensors. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the hardware processor 602, the main memory 604, the static memory 606, or the mass storage 608 may be, or include, a machine-readable medium 622 on which is stored one or more sets of data structures or instructions 624 (e.g., software) embodying or utilized by any one or more of the techniques or functions described herein. The instructions 624 may also reside, completely or at least partially, within any of registers of the hardware processor 602, the main memory 604, the static memory 606, or the mass storage 608 during execution thereof by the machine 600. In an example, one or any combination of the hardware processor 602, the main memory 604, the static memory 606, or the mass storage 608 may constitute the machine-readable medium 622. While the machine-readable medium 622 is illustrated as a single medium, the term "machine-readable medium" may include a single medium or multiple media (e.g., a centralized or distributed database, and/or associated caches and servers) configured to store the one or more instructions 624.

The term "machine-readable medium" may include any medium that is capable of storing, encoding, or carrying instructions for execution by the machine 600 and that cause the machine 600 to perform any one or more of the techniques of the present disclosure, or that is capable of storing, encoding, or carrying data structures used by or associated with such instructions. Non-limiting machine-readable medium examples may include solid-state memories, optical media, magnetic media, and signals (e.g., radio frequency signals, other photon-based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may be further transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 602.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 600, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A medical device system, comprising:

a signal receiver circuit configured to receive cardiac acceleration information of a patient, wherein the cardiac acceleration information is determined using an accelerometer or a microphone; and an assessment circuit configured to detect a potential syncope event in a first low-power mode using the cardiac acceleration information of the patient, and to transition a medical device of the medical device system from the first low-power mode to a second high-power mode in response to the detected potential syncope event, wherein to detect the potential syncope event, the assessment circuit is configured to compare the cardiac acceleration information to at least one threshold, and to transition the medical device to the second high-power mode comprises in response to the cardiac acceleration information exceeding the at least one threshold.

2. The system of claim 1, wherein the signal receiver circuit is configured to receive cardiac electrical information of the patient, and wherein the assessment circuit is configured to detect the potential syncope event using the cardiac acceleration information and the cardiac electrical information of the patient.

3. The system of claim 2, wherein the cardiac acceleration information comprises heart sound information of the patient, wherein the cardiac electrical information of the patient comprises heart rate information of the patient, and wherein the assessment circuit is configured to detect the potential syncope event using an increase in first heart sound (S1) information of the patient greater than a first threshold and an increase in the heart rate information of the patient greater than a second threshold.

4. The system of claim 3, wherein the assessment circuit is configured to detect an indication of a neurally mediated syncope (NMS) event using a decrease in second heart sound (S2) information of the patient greater than a third threshold in a first time period following the detected potential syncope event.

5. The system of claim 4, wherein the assessment circuit is configured to detect the indication of the NMS event using the decrease in S2 information of the patient greater than the third threshold and a decrease in the S1 information of the patient greater than a fourth threshold in the first time period following the detected potential syncope event, and a subsequent decrease in the heart rate information greater than a fifth threshold in a second time period following the first time period.

6. The system of claim 4, wherein the assessment circuit is configured to trigger a patient alert indicative of the detected indication of the NMS event and a patient inquiry to receive patient feedback of the detected indication of the NMS event in response to the detected indication of the NMS event.

7. The system of claim 4, comprising:

a therapy circuit configured to alter or provide one of a drug therapy or a pacing therapy in response to the detected indication of the NMS event.

8. The system of claim 2, wherein the signal receiver circuit is configured to receive activity or posture information of the patient, and wherein the assessment circuit is configured to detect a high risk syncope position of the patient using the activity or posture information of the patient, and in response to the detected high risk syncope position, to detect the potential syncope event using an increase in the cardiac acceleration information greater than a first threshold and an increase in the cardiac electrical information greater than a second threshold.

9. The system of claim 8, wherein the assessment circuit is configured to detect the high risk syncope position of the patient as:

a detected change in patient posture from a horizontal thoracic position to a vertical thoracic position; or a detected vertical thoracic position and patient activity information below an activity threshold.

10. The system of claim 8, wherein the signal receiver circuit is configured to receive the cardiac acceleration information and activity or posture information of the patient using a signal accelerometer in non-overlapping time periods.

11. The system of claim 2, wherein the first low-power mode comprises an ambulatory monitoring mode, wherein the second high-power mode comprises a higher-power monitoring mode including storing received cardiac acceleration information and the received cardiac electrical information in long-term storage, and wherein the medical device comprises an implantable medical device comprising the signal receiver circuit and the assessment circuit.

12. The system of claim 1, wherein the cardiac acceleration information comprises heart sound information of the patient, wherein the assessment circuit is configured to determine, in the second high-power mode, a composite heart sound parameter including first heart sound (S1) information of the patient over second heart sound (S2) information of the patient, (S1/S2), and to detect an indication of a syncope event in the second high-power mode using the determined composite heart sound parameter.

13. The system of claim 1, wherein the assessment circuit is configured to store, in the low-power mode, received cardiac acceleration information in short-term storage, and to store, in the second high-power mode, sequential time-period windows of the received cardiac acceleration information leading up to and including the detected potential syncope event in long-term storage.

14. The system of claim 1, wherein the assessment circuit is configured to detect the potential syncope event using an increase in first heart sound (S1) of the patient greater than a first threshold and an increase in the second heart sound (S2) information of the patient greater than a second threshold.

15. A method comprising:

receiving, using a signal receiver circuit, cardiac acceleration information of a patient, wherein the cardiac acceleration information is determined using an accelerometer or a microphone;

detecting, using an assessment circuit in a first low-power mode, a potential syncope event using the cardiac acceleration information of the patient; and transitioning, using the assessment circuit, a medical device from the first low-power mode to a second high-power mode in response to the detected potential syncope event, wherein detecting the potential syncope event comprises comparing the cardiac acceleration information to at least one threshold and transitioning the medical device to the second high-power mode comprises in response to the cardiac acceleration information exceeding the at least one threshold.

16. The method of claim 15, comprising:

receiving, using the signal receiver circuit, cardiac electrical information of the patient, wherein detecting the potential syncope event comprises using the cardiac acceleration information and the cardiac electrical information of the patient.

17. The method of claim 16, wherein the cardiac acceleration information comprises heart sound information of the patient, wherein the cardiac electrical information of the patient comprises heart rate information of the patient, and wherein detecting the potential syncope event comprises using an increase in first heart sound (S1) information of the patient greater than a first threshold and an increase in the heart rate information of the patient greater than a second threshold.

18. The method of claim 17, comprising:

detecting, using the assessment circuit, an indication of a neurally mediated syncope (NMS) event using a decrease in second heart sound (S2) information of the patient greater than a third threshold in a first time period following the detected potential syncope event.

19. The method of claim 18, wherein detecting the indication of the NMS event comprises using the decrease in S2 information of the patient greater than the third threshold and a decrease in the S1 information of the patient greater than a fourth threshold in the first time period following the detected potential syncope event, and using a subsequent decrease in the heart rate information greater than a fifth threshold in a second time period following the first time period.

20. The method of claim 16, comprising:

receiving, using the signal receiver circuit, activity or posture information of the patient; and detecting, using the assessment circuit, a high risk syncope position of the patient using the activity or posture information of the patient, wherein detecting the potential syncope event comprises using an increase in the cardiac acceleration information greater than a first threshold and an increase in the cardiac electrical information greater than a second threshold, further in response to the detected high risk syncope position, wherein detecting the high risk syncope position of the patient comprises using:

a detected change in patient posture from a horizontal thoracic position to a vertical thoracic position; or a detected vertical thoracic position and patient activity information below an activity threshold.

* * * * *